United States Patent [19]

Goetz et al.

[11] 3,932,462

[45] Jan. 13, 1976

[54] MANUFACTURE OF UNSATURATED KETONES

[75] Inventors: Norbert Goetz, Bobenheim-Roxheim; Roman Fischer, Mutterstadt, both of Germany

[73] Assignee: BASF Aktiengesellschaft, Ludwigshafen (Rhine), Germany

[22] Filed: Nov. 13, 1973

[21] Appl. No.: 415,414

[30] Foreign Application Priority Data

Nov. 17, 1972 Germany............................ 2256347

[52] U.S. Cl....... 260/340.7; 260/586 C; 260/590 R; 260/593 R
[51] Int. Cl.$^2$...................................... C07D 319/06
[58] Field of Search............ 260/590, 590 R, 586 C, 260/593 R, 340.7

[56] References Cited

UNITED STATES PATENTS 3,655,768  4/1972  Pommer et al. ................ 260/590 X

*Primary Examiner*—Anton H. Sutto
*Attorney, Agent, or Firm*—Johnston Keil, Thompson & Shurtleff

[57] ABSTRACT

Manufacture of high molecular weight unsaturated ketones by reacting allyl alcohols with 1-substituted butadiene-1-alkyl ethers or with 1-substituted butadiene-1-alkyl esters or with substances capable of forming said compounds under the conditions of the reaction, in the presence of acid catalysts at elevated temperatures and in the liquid phase. The resulting unsaturated ketones are precursors or intermediates in the manufacture of a variety of natural dyes such as zeaxanthin, rhodoxanthin and xanthophyll or of odorants such as damascones and damascenones.

11 Claims, No Drawings

MANUFACTURE OF UNSATURATED KETONES

This invention relates to a process for the manufacture of high molecular weight unsaturated ketones by reacting allyl alcohols with 1-substituted butadiene-1-alkyl ethers or with 1-substituted butadiene-1-alkyl esters or with substances capable of forming these compounds under the conditions of the reaction, in the presence of acid catalysts at elevated temperatures and in the liquid phase.

German published application No. 1,768,552 describes the manufacture of unsaturated aldehydes by reacting allyl alcohols with 1-unsubstituted butadiene-1-alkyl ethers or compounds capable of forming such butadiene-1-alkyl ethers under the conditions of the reaction. The reaction is mainly carried out at 100°C using a catalyst system consisting of sodium acetate and mercury acetate. The yields of unsaturated aldehydes obtained in this process are generally unsatisfactory. Furthermore, the use of mercury acetate as catalyst involves serious purifying problems.

We have now found that α,β-unsaturated ketones of the general formula I:

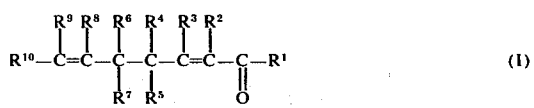
(I)

in which $R^1$ is alkyl of from 1 to 4 carbon atoms, preferably methyl, a cycloaliphatic group or unsubstituted or alkyl-substituted phenyl or $R^1$, together with $R^4$ or $R^5$, is unsubstituted or alkyl-substituted alkylene, $R^2$, $R^3$, $R^4$, $R^5$, $R^6$, $R^7$ and $R^8$ are hydrogen or alkyl of from 1 to 4 carbon atoms, preferably hydrogen or methyl, $R^9$ is alkyl of from 1 to 4 carbon atoms, preferably methyl, or, when $R^{10}$ is phenyl, $R^9$ stands for hydrogen, and $R^{10}$ is a saturated or unsaturated, branched or unbranched aliphatic, cycloaliphatic or cycloaliphatic/aliphatic hydrocarbon radical of up to 12 carbons in which C—C bonds may be interrupted by oxygen or the group —O—CO—, or unsubstituted or alkyl-substituted phenyl, may be obtained in a simple manner and in very good yields when an allyl alcohol of formula II:

(II)

in which $R^6$ to $R^{10}$ have the meanings stated above, is reacted with a compound of the formula IIIa:

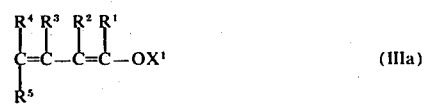
(IIIa)

in which $R^1$ to $R^5$ have the meanings stated above and $X^1$ is straight-chain or branched-chain alkyl or acyl of from 1 to 6 carbon atoms or a cycloaliphatic radical, or with a compound capable of forming a compound of formula IIIa under the conditions of the reaction, at temperatures of from 120° to 350°C and preferably from 140° to 290°C in the presence of from 0.01 to 5% and preferably from 0.1 to 3% by weight of the total weight of reactants of an acid having a pK value of from 1 to 5.5 or in the presence of from 0.001 to 0.1% and preferably from 0.005 to 0.05% by weight of the total weight of reactants of an acid having a pK value of less than 1, in the liquid phase.

Suitable compounds capable of forming compounds of formula IIIa under the conditions of the reaction are, for the purpose of the invention, compounds of formulae IIIb and IIIc:

(IIIb)

(IIIc)

in which $R^1$ to $R^5$ have the meanings stated above and $X^1$ and $X^2$ are the same or different and denote straight-chain or branched-chain alkyl or acyl of from 1 to 6 carbon atoms or a cycloaliphatic hydrocarbon radical or alternatively together form unsubstituted or alkyl-substituted alkylene, and also compounds of formula IIId:

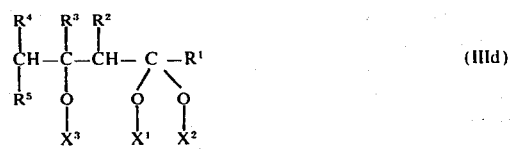
(IIId)

in which $R^1$ to $R^5$ have the meanings stated above and $X^1$, $X^2$ and $X^3$ may be the same or different and are straight-chain or branched-chain alkyl or acyl of from 1 to 6 carbon atoms or cycloaliphatic hydrocarbon radicals, or $X^1$ and $X^2$ together form an unsubstituted or alkyl-substituted alkylene radical.

It is surprising that not only the highly reactive 1-unsubstituted butadiene-1-alkyl ethers react with allyl alcohols but also the generally very much less reactive 1-substituted butadiene-1-alkyl ethers and butadiene-1-alkyl esters, i.e., enol derivatives of unsaturated ketones, react with allyl alcohols in the manner described. Other unexpected results are that the reaction of the 1-substituted butadiene-1-alkyl ethers or esters or the reaction of the compounds capable of forming such butadiene compounds under the conditions of the reaction with ally alcohols produces higher molecular weight unsaturated ketones of formula I, and that the yields are so good that these ketones can be advantageously produced thereby on an industrial scale.

In the process of the invention, the allyl alcohols of formula II used are preferably those having a total of from 5 to 20 carbon atoms and in particular from 5 to 15 carbon atoms.

Examples thereof are 3-methyl-2-buten-1-ol, 3-methyl-2-penten-1-ol, cyclic acetals of 4-hydroxy-2-methyl-2-buten-1-al, 4-methoxy-3-methyl-2-buten-1-ol, 4-acetoxy-3-methyl-2-buten-1-ol, 4-methyl-3-penten-2-ol, 1,1,3-trimethyl-3-cyclohexen-5-ol, geraniol, nerol, farnesol and 3-methylcinnamyl alcohol.

Examples of suitable compounds of formula IIIa are the following butadiene-1-alkyl ethers or esters: 4-methyl-2,4-pentadien-2-yl acetate, 1,1,5-trimethyl-3-ethoxy-3,5-cyclohexadiene, 6-methyl-2,4,6-heptatrien-2-yl acetate, 4,8-dimethyl-2-methoxy-2,4,7-nonatriene and 6,10-dimethyl-2-ethoxy-2,4,6,9-undecatetraene.

The enol ethers of formula IIIa may be produced by known methods, for example by reacting the corresponding acetylene compounds with alcohols or by the elimination of alcohols from ketals. The enol esters of formula IIIa may be produced by adding carboxylic acids to the corresponding acetylene compounds or, in the case of acetates, by reacting the ketones with ketene or transesterification with isopropylene acetate.

Example of suitable compounds of formula IIIb are 4-methyl-2,2-diacetoxy-3-pentene, 2-methyl-2-(2'-methyl-1'-propene-1'-yl)-1,3-dioxolane, 1,1,5-trimethyl-3,3-diacetoxy-4-cyclohexene, 4-methyl-2,2-di-n-propoxy-3-pentene and 6,10-dimethyl-2,2-dimethoxy-3,5,9-undecatriene.

The ketals of formula IIIb may be prepared by reacting ketones with alcohols in the presence of orthoesters followed by transketalization with acetone dimethylketal. The corresponding esters are formed by treatment of ketals with carboxylic anhydrides.

Suitable compounds of formula IIIc are for example 1,1,5-trimethyl-3,3-diethoxy-5-cyclohexene, 4-methyl-2,2-diethoxy-4-pentene and 4-methyl-2,2-diacetoxy-4-pentene.

The ketals or esters of formula IIIc may be prepared by isomerization of ketals or esters of formula IIIb.

Examples of suitable compound of formula IIIb are 4-methyl-2,2,4-triethoxypentane, 4-methyl-2,2,4-trimethoxypentane, the ketal of 4-methyl-4-(2'-hydroxyethoxy)pentan-2-one with ethylene glycol and 1,1,5-trimethyl-3,3,5-triacetoxycyclohexane.

The trialkoxy compounds may be manufactured by reacting unsaturated ketones with alcohols in the presence of strong acids. The corresponding esters are obtained by treating the trialkoxy compounds with carboxylic anhydrides.

Mixed alkoxy/acyloxy compounds may be obtained by transketalization with alcohols or reaction with carboxylic anhydrides.

Suitable catalysts for use in the reaction of the invention are virtually all compounds which donate protons and do not otherwise attack the reactants when used in the amounts necessary for catalysis. Since some of the starting materials and reaction products are sensitive to acids, it is important that the reaction mixture should not produce an unduly acid reaction. Best results are obtained using a reaction mixture to which sufficient acid has been added to give a pH of from about 1 to 6 and preferably from 2 to 5 when measured with a commercial pH paper dipped into the reaction mixture. The reaction of the invention proceeds in a particularly advantageous manner when carried out in the presence of from 0.01 to 5% and preferably from 0.1 to 3% by weight of the total weight of reactants of an acid having a pK value of from about 1 to 5.5.

These preferred acids having a pK value of from about 1 to 5.5 are substantially carboxylic acids. Examples thereof are formic acid, acetic acid, propionic acid, benzoic acid, acrylic acid, dimethylacrylic acid, oxalic acid, malonic acid, succinic acid and adipic acid.

In the case of a number of carboxylic acids used as catalyst, special advantages are obtained when working up the reaction mixture. For example, the low-boiling carboxylic acids such as formic acid, acetic acid, propionic acid, butyric acid, isobutyric acid, acrylic acid and dimethylacrylic acid may be readily removed from the reaction mixture by distillation. High-boiling carboxylic acids, such as adipic acid, glutaric acid, pimelic acid, suberic acid and stearic acid, are so weakly acid (pK 4–5.5) that there is no need to remove or neutralize them before working up by distillation. Thus in both cases there is no need to neutralize the catalytic acid, which means that industrial operation of the process is greatly simplified and waste water problems are avoided.

Whe use is made of stronger acids, i.e., acids having a pK value of less than 1, only small amounts of acid can be employed on account of the said sensitivity of the compounds used to acids. The reaction of the invention proceeds in an advantageous manner when carried out in the presence of from 0.001 to 0.1% and preferably from 0.005 to 0.05% by weight of the total weight of reactants of an acid having a pK value of less than 1.

Examples of such acids having a pK value of less than 1 are sulfuric acid, p-toluenesulfonic acid, the haloacetic acids, the hydrohalogenic acids and phosphoric acid.

Less suitable is the use of very weakly acidic compounds, i.e., acids having a pK value of less than 7, as in the case of the phenols.

The process is generally carried out by heating a mixture of the starting components with the acid catalyst to the reaction temperature for the duration of the reaction, if necessary under superatmospheric pressure and/or with vigorous agitation.

The starting components may be used in stoichiometric amounts. Alternatively, it is possible to use one of the two components, preferably the more stable component, in an excess of from 1 to 4 moles.

The reaction of the invention is carried out at temperatures of from about 120° to 350°C and preferably from 140° to 290°C.

The process may be carried out at atmospheric pressure or at a pressure of up to 250 atmospheres. The reaction conditions are chosen so that the reaction always takes place in the liquid phase.

The reaction time in the process of the invention depends on the reaction temperature and the catalyst used and is from 5 minutes to 20 hours, preferably from 30 minutes to 10 hours.

The reaction may be carried out in the presence or absence of solvents.

Suitable solvents are aliphatic and aromatic hydrocarbons which are inert under the conditions of the reaction, for example hexane, heptane, benzene, toluene and xylene, and also ethers, e.g., tetrahydrofuran, dioxane and 1,2-dimethoxyethane, and, in particular, strongly polar solvents such as acetonitrile, dimethyl formamide and dimethyl sulfoxide.

The solvents, when used, are employed in an amount of from 1 to 5 times the total weight of the starting components.

The process may be carried out batchwise in a stirred vessel or vibratory autoclave or continuously in a reactor or cascade of reactors.

The reaction may be favorably influenced by continuously removing from the reaction mixture the alcohol or acid which is formed during the reaction.

The reaction mixture is generally worked up by fractional distillation.

The process of the invention produces, in a simple manner and in very good yields, a number of high molecular weight α,β-unsaturated ketones which have hitherto been prepared only by means of expensive processes and which may be used as valuable precursors or intermediates in the manufacture of a variety of natural dyes such as zeaxanthin, rhodoxanthin and xanthophyll or odorants such as the damascones or damascenones.

For example, the acetals of -(3'-formyl-2'-butenyl)-2,2,6-trimethylcyclohex-5-en-4-one which can be produced by the process of the invention from 1,1,5-trimethyl-3-ethoxy-3,5-cyclohexadiene and acetals of β-formylcrotyl alcohol are valuable intermediates in the manufacture of rhodoxanthin. The manufacture of rhodoxanthin from the said acetals may take place by converting the oxo group to a hydroxyl group by means of LiAlH$_4$, acid hydrolysis, vinylation, reaction with triphenylphosphonium bromide in methanol to form the 6-[2', 2', 6'-trimethyl-4'-hydroxy-5'-cyclohexen-1'-yl]-4-methyl-2,4-hexadien-1-yl-triphenylphosphonium bromide, effecting a Wittig reaction with 2,7-dioxo-3,5-octadiene followed by dehydrogenation of the resulting carotinoid.

In the following Examples the parts are by weight unless otherwise stated.

EXAMPLE 1

A mixture of 25 parts of 4-methyl-2,2-diacetoxy-3-pentene, 10 parts of 3-methyl-2-buten-1-ol (prenol) and 0.3 part of propionic acid is heated for 3 hours at about 200°C in a vibratory autoclave at a pressure 30 atmospheres. After cooling, the reaction product is distilled off to give 9.4 parts of 4,8-dimethyl-3,7-nonadien-2-one having a boiling point of 60°–62°C/0.2 mm. The yield is 81% of theory at a conversion of 60% based on the prenol introduced.

EXAMPLE 2

110 parts of 4-methyl-2,4-pentadien-2-yl acetate and 60 parts of prenol are heated with 1.4 parts of 3,3-dimethylacrylic acid at about 180°C for 4 hours in a small pressure column at a pressure of 2 atmospheres, the acetic acid formed being distilled off continuously. Fractional distillation of the reaction product gives 61.8 parts of 4,8-dimethyl-3,7-nonadien-2-one (yield 86% of theory, conversion 62% based on prenol).

EXAMPLE 3

A mixture of 20 parts of 2-methyl-2-(2'-methyl-1'-propen-1'-yl)-1,3-dioxolane (ketal of mesityl oxide with ethylene glycol), 10 parts of geraniol and 0.15 part of benzoic acid is prepared and heated for 5 hours at 190°C under a pressure of approximately 1.8 atmospheres. Fractional distillation of the reaction product is 8.2 parts of 4,8,12-trimethyl-3,7,11-decatrien-2-one having a boiling point of 92°–94°C/10$^{-4}$ mm (yield 88% of theory, conversion 61% based on geraniol).

EXAMPLE 4

100 parts of 1,1,5-trimethyl-3,3-diacetoxy-4-cyclohexene, 50 parts of prenol and 3 parts of 3,3-dimethylacrylic acid are heated at 185°C for 3 hours at a pressure of 2 atmospheres, the acetic acid formed being distilled off under pressure. Fractional distillation of the reaction product gives 66.3 parts of 1-(3'-methyl-2'-buten-1'-yl)-2,2,6-trimethylcyclohex-5-en-4-one having a boiling point of 75°–76°C/10$^{-4}$ mm (yield 84% of theory, conversion 64% based on prenol).

EXAMPLE 5

In a flask equipped with a stirrer and fitted with a column a mixture of 80 parts of 1,1,5-trimethyl-3-ethoxy-3,5-cyclohexadiene, 40 parts of the acetal of 2-methyl-4-hydroxy-2-buten-1-al (β-formylcrotyl alcohol) with neopentyl glycol and 1.2 parts of benzoic acid is heated for 3 hours at 180°C, the ethyl alcohol formed during the reaction being distilled off continuously. Fractional distillation of the reaction product gives 33.6 parts of the acetal of 1-(3'-formyl-2'-butenyl)-2,2,6-trimethylcyclohex-5-en-4-one with neopentyl glycol having a boiling point of 140°–143°C/10$^{-4}$ mm (yield 81% of theory, conversion 63% based on the acetal of β-formylcrotyl alcohol with neopentyl glycol).

EXAMPLE 6

A mixture of 100 parts of 4-methyl-2,2,4-triethoxypentane, 40 parts of prenol and 0.08 part of p-toluenesulfonic acid is heated for 6 hours at 140°C, the ethyl alcohol formed being distilled off continuously. On completion of the reaction, the reaction mixture is neutralized with sodium ethoxide and the reaction product is fractionally distilled. There are obtained 45.2 parts of 4,8-dimethyl-3,7-nonadien-2-one, equivalent to a yield of 86% and a conversion of 68% based on prenol.

EXAMPLE 7

80 parts of 1,1,5-trimethyl-3,3-diethoxy-5-cyclohexene and 30 parts of prenol are heated with 0.1 part of oxalic acid for 6 hours at 140°C, the ethyl alcohol formed being distilled off continuously. After neutralization and fractional distillation, there are obtained 45 parts of 1-(3'-methyl-2'-buten-1'-yl)-2,6,6-trimethyl-5-cyclohexen-4-one at a yield of 88% and a conversion of 71% based on prenol.

EXAMPLE 8

In an autoclave, a mixture of 120 parts of 4-methyl-2,2-di-n-propoxy-4-pentene, 50 parts of prenol and 170 parts of cyclohexane is heated with 3.4 parts of formic acid for 4 hours at 160°C. Fractional distillation gives 57.5 parts of 4,8-dimethyl-3,7-nonadien-2-one, equivalent to a yield of 89% and a conversion of 67% based on prenol.

We claim:

1. A process for the manufacture of α,β-unsaturated ketones of the formula I:

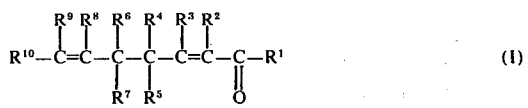

in which R$^1$ is alkyl of from 1 to 4 carbon atoms, or R$^1$, together with R$^4$ or R$^5$, forms unsubstituted or alkyl-substituted alkylene, R$^2$, R$^3$, R$^4$, R$^5$, R$^6$, R$^7$ and R$^8$ are hydrogen or alkyl of from 1 to 4 carbon atoms, R$^9$ is alkyl of 1 to 4 carbon atoms or, when R$^{10}$ is phenyl, R$^9$ is hydrogen, and R$^{10}$ is a saturated or unsaturated, branched or unbranched aliphatic, cycloaliphatic or cycloaliphatic/aliphatic hydrocarbon radical of up to 12 carbons in which C—C bonds may be interrupted by oxygen or the group —O—CO—, or unsubstituted phenyl, wherein an allyl alcohol of the formula II:

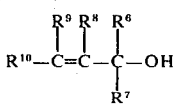  (II)

in which $R^6$ to $R^{10}$ have the meanings stated above, is reacted with a compound of the formula IIIa:

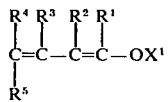  (IIIa)

in which $R^1$ to $R^5$ have the meanings stated above and $X^1$ is alkyl or acyl of from 1 to 6 carbons or cycloalkyl, or with a compound capable of forming a compound of formula IIIa under the conditions of the reactions, said compound being selected from the group consisting of a compound of the formulae

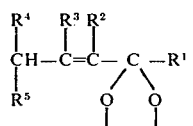

(IIIb)

(IIIc)

,and (IIId)

in which formulae IIIb, c and d $R^1$ to $R^5$ have the meanings given above and $X^2$, $X^3$ and $X^4$ may be the same or different and stand for alkyl or acyl of from 1 to 6 carbon atoms or cycloalkyl or $X^4$ and $X^2$ together form unsubstituted or alkyl-substituted alkylene at temperatures of from 120° to 350° in the presence of from 0.01 to 5% by weight of the total weight of reactants of an acid having a pK value of from 1 to 5.5 or in the presence of from 0.001 to 0.1% by weight of the total weight of reactants of an acid having a pk value of less than 1, in the liquid phase.

2. A process as claimed in claim 1, wherein the allyl alcohol of formula II is reacted with a compound of formula IIIb:

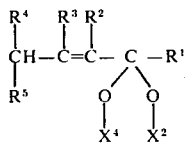  (IIIb)

in which $R^1$ to $R^5$ have the meanings stated in claim 1 and $X^4$ and $X^2$ are the same or different and are alkyl or acyl of from 1 to 6 carbon atoms or cycloalkyl or together form unsubstituted or alkyl-substituted alkylene, as the compound capable of forming a compound of formula IIIa under the conditions of the reaction.

3. A process as claimed in claim 1, wherein the allyl alcohol of formula II is reacted with a compound of formula IIIc:

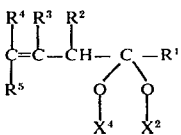  (IIIc)

in which $R^1$ to $R^5$ have the meanings stated in claim 1 and $X^4$ and $X^2$ may be the same or different and stand for alkyl or acyl of from 1 to 6 carbon atoms or cycloalkyl or together form unsubstituted or alkyl-substituted alkylene, as the compound capable of forming a compound of formula IIIa under the conditions of the reaction.

4. A process as claimed in claim 1, wherein the allyl alcohol of formula II is reacted with a compound of formula IIId:

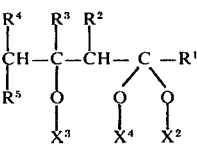  (IIId)

in which $R^1$ to $R^5$ have the meanings stated in claim 1 and $X^4$, $X^2$ and $X^3$ may be the same or different and stand for alkyl or acyl of from 1 to 6 carbon atoms or cycloalkyl or $X^1$ and $X^2$ together form unsubstituted or alkyl-substituted alkylene, as the compound capable of forming a compound of formula IIIa under the conditions of the reaction.

5. A process as claimed in claim 1, wherein the alcohol or acid formed during the reaction is continuously removed from the reaction mixture.

6. A process as claimed in claim 1, wherein the reaction is carried out at temperatures of from 130° to 290°C.

7. A process for the production of 1-(3-methyl-2'-buten-1'-yl)2,2,6-trimethyl-5-cyclohex-4-one which comprises reacting prenol and 1,1,5-trimethyl-3,3-diethoxy-5-cyclohexene at temperatures of from 120° to 350°C. in the presence of from 0.01 to 5% by weight of the total weight of reactants of an acid having a pK value of from 1 to 5.5 or in the presence of from 0.001 to 0.1% by weight of the total weight of reactants of an acid having a pK value of less than 1, in the liquid phase.

8. A process for the production of 4,8,12-trimethyl-3,7,11-decatrien-2-one which comprises reacting gerianol and 2-methyl-2-(2'-methyl-1'-propen-1'-yl)-1,3-dioxolane at temperatures of from 120° to 350°C. in the presence of from 0.01 to 5% by weight of the total weight of reactants of an acid having a pK value of from 1 to 5.5 or in the presence of from 0.001 to 0.1% by weight of the total weight of reactants of an acid having a pK value of less than 1, in the liquid phase.

9. A process for the production of the acetal of 1-(3'-formyl-2'-butenyl)-2,2,6-trimethylcyclohex-5-en-4-one with neopentyl glycol which comprises reacting 1,1,5-trimethyl-3-ethoxy-3,5-cyclohexadiene and the acetal of 2-methyl-4-hydroxy-2-buten-1-al with neopentyl glycol at temperatures of from 120° to 350°C. in the presence of from 0.01 to 5% by weight of the total weight of reactants of an acid having a pK value of from 1 to 5.5 or in the presence of from 0.001 to 0.1% by weight of the total weight of reactants of an acid having a pK value of less than 1, in the liquid phase.

10. A process for the production of 4,8-dimethyl-3,7-nonadien-2-one which comprises reacting prenol and 4-methyl-2,2,4-triethoxypentane at temperatures of from 120° to 350°C in the presence of from 0.01 to 5% by weight of the total weight of reactants of an acid having a pK value of from 1 to 5.5 or in the presence of from 0.001 to 0.1% by weight of the total weight of reactants of an acid having a pK value of less than 1, in the liquid phase.

11. A process for the production of 4,8-dimethyl-3,7-nonadien-3-one which comprises reacting prenol and 4-methyl-2,2-di-n-propoxy-4-pentene at temperatures of from 120° to 350°C. in the presence of from 0.01 to 5% by weight of the total weight of reactants of an acid having a pK value of from 1 to 5.5 or in the presence of from 0.001 to 0.1% by weight of the total weight of reactants of an acid having a pK value of less than 1, in the liquid phase.

* * * * *